United States Patent
Leuthardt et al.

(10) Patent No.: US 10,625,068 B2
(45) Date of Patent: Apr. 21, 2020

(54) BREAKAWAY CONNECTOR

(71) Applicant: WASHINGTON UNIVERSITY, St. Louis, MO (US)

(72) Inventors: Eric Leuthardt, St. Louis, MO (US); Guy Genin, St. Louis, MO (US); Eric Arias, St. Louis, MO (US); James Norlin, St. Louis, MO (US); Brittany Scheid, St. Louis, MO (US); Chandu Vemuri, St. Louis, MO (US); Ralph Dacey, St. Louis, MO (US); Colin Derdeyn, St. Louis, MO (US); Gregory Zipfel, St. Louis, MO (US); Albert Kim, St. Louis, MO (US); Philip Bayly, St. Louis, MO (US); Srikanth Singamaneni, St. Louis, MO (US); Lihong Wang, St. Louis, MO (US)

(73) Assignee: Washington University, St. Louis, MO (US)

( * ) Notice: Subject to any disclaimer, the term of this patent is extended or adjusted under 35 U.S.C. 154(b) by 249 days.

(21) Appl. No.: 15/553,450

(22) PCT Filed: Feb. 23, 2016

(86) PCT No.: PCT/US2016/019171
§ 371 (c)(1),
(2) Date: Aug. 24, 2017

(87) PCT Pub. No.: WO2016/138022
PCT Pub. Date: Sep. 1, 2016

(65) Prior Publication Data
US 2018/0243546 A1 Aug. 30, 2018

Related U.S. Application Data

(60) Provisional application No. 62/120,622, filed on Feb. 25, 2015.

(51) Int. Cl.
*A61M 39/10* (2006.01)
*A61M 39/22* (2006.01)
(Continued)

(52) U.S. Cl.
CPC ........ *A61M 39/10* (2013.01); *A61M 39/1011* (2013.01); *A61M 39/22* (2013.01);
(Continued)

(58) Field of Classification Search
CPC .. A61M 39/10; A61M 39/1011; A61M 39/26; A61M 2039/1027; F16L 55/1007; F16L 55/1015
See application file for complete search history.

(56) References Cited

U.S. PATENT DOCUMENTS

| 3,921,656 A | 11/1975 | Meisenheimer, Jr. et al. |
| 4,232,697 A | 11/1980 | Meisenheimer, Jr. |

(Continued)

FOREIGN PATENT DOCUMENTS

WO 2013016623 A2 1/2013

OTHER PUBLICATIONS

International Search Report and Written Opinion of the International Searching Authority regarding PCT/US2016/019171 dated Jul. 7, 2016; 7 pgs.

*Primary Examiner* — Nathan R Price
*Assistant Examiner* — Anh Bui
(74) *Attorney, Agent, or Firm* — Armstrong Teasdale LLP

(57) ABSTRACT

A breakaway connector generally includes a first valve having a first rotating-type fluid control member, and a second valve that is attachable to the first valve and has a second rotating-type fluid control member. Each of the fluid control members has an open position in which fluid is permitted to flow through the respective valve, and a closed position in which fluid is prevented from flowing through (Continued)

the respective valve. Each one of the valves is configured to engage the fluid control member of the other one of the valves to move the fluid control member from the open position to the closed position upon detachment of the valves from one another.

19 Claims, 10 Drawing Sheets

(51) Int. Cl.
*F16L 55/10* (2006.01)
*A61M 39/26* (2006.01)

(52) U.S. Cl.
CPC ......... *A61M 39/26* (2013.01); *F16L 55/1007* (2013.01); *F16L 55/1015* (2013.01); *A61M 2039/1027* (2013.01); *A61M 2039/1044* (2013.01); *A61M 2039/1061* (2013.01); *A61M 2039/226* (2013.01); *A61M 2039/261* (2013.01); *A61M 2039/262* (2013.01); *A61M 2039/263* (2013.01); *A61M 2039/265* (2013.01); *A61M 2039/266* (2013.01); *A61M 2039/267* (2013.01); *A61M 2039/268* (2013.01)

(56) References Cited

U.S. PATENT DOCUMENTS

| | | | |
|---|---|---|---|
| 4,296,914 A | | 10/1981 | Allread |
| 4,301,823 A | | 11/1981 | Meisenheimer, Jr. |
| 4,328,822 A | | 5/1982 | Wilhelm |
| 4,351,351 A | * | 9/1982 | Flory ................. F16L 55/1015 137/614.03 |
| 4,351,352 A | * | 9/1982 | Meisenheimer, Jr. ..................... F16L 55/1007 137/15.09 |
| 4,361,165 A | | 11/1982 | Flory |
| 4,643,216 A | | 2/1987 | Allread et al. |
| 4,646,773 A | | 3/1987 | Klop et al. |
| 4,690,675 A | | 9/1987 | Katz |
| 4,905,733 A | | 3/1990 | Carow |
| 5,209,262 A | | 5/1993 | Carow et al. |
| 5,305,776 A | | 4/1994 | Romano |
| 5,314,411 A | | 5/1994 | Bierman et al. |
| 5,320,133 A | | 6/1994 | Nimberger |
| 5,599,311 A | | 2/1997 | Raulerson |
| 5,791,366 A | | 8/1998 | Lo |
| 6,258,066 B1 | | 7/2001 | Urich |
| 7,163,531 B2 | | 1/2007 | Seese et al. |
| 7,678,101 B2 | | 3/2010 | Sage |
| 7,766,394 B2 | | 8/2010 | Sage et al. |
| 8,197,447 B2 | | 6/2012 | Wright |
| 2008/0172003 A1 | * | 7/2008 | Plishka ............... A61M 39/045 604/249 |
| 2012/0010515 A1 | | 1/2012 | Zhou et al. |
| 2013/0030387 A1 | * | 1/2013 | Williams ........... A61M 39/1011 604/256 |
| 2013/0125989 A1 | | 5/2013 | Clever et al. |
| 2014/0179170 A1 | | 6/2014 | De Jong et al. |

* cited by examiner

BREAKAWAY CONNECTOR

This application is a U.S. National Phase Application of PCT/US2016/019171, filed on Feb. 23, 2016, which claims the benefit of claims the benefit of U.S. Provisional Application No. 62/120,622 filed Feb. 25, 2015, which are incorporated herein by reference in their entirety.

CROSS-REFERENCE TO RELATED APPLICATION

This application claims the benefit of U.S. Provisional Application No. 62/120,622 filed Feb. 25, 2015, which is incorporated herein by reference in its entirety.

BACKGROUND

The present disclosure relates generally to breakaway connectors and, more particularly, to a breakaway connector for use in clinical settings.

It is common for a patient in a clinical setting to receive catheterization treatment, during which a tube is inserted into a cavity, duct, or vessel of the patient when administering fluids to the patient or draining fluids from the patient. To maintain proper insertion of the tube in the patient, the tube is often fastened to the patient's body, using tape for example. However, because the tube typically hangs loosely in its extension to a nearby fluid reservoir, the tube can become caught on adjacent people or devices while the patient is being treated, thereby causing the tube to pull away from the patient. This can result in the tube being damaged and/or removed from the patient, which in turn can cause discomfort to the patient and can require replacement and/or reinsertion of the tube, not to mention the possible loss of fluid from the fluid system or the loss of sterility in the fluid system.

There is a need, therefore, for a breakaway connector that permits detachment of a tube under the influence of an external pulling force.

SUMMARY

In one aspect, a breakaway connector generally comprises a first valve having a first rotating-type fluid control member, and a second valve that is attachable to the first valve and has a second rotating-type fluid control member. Each of the fluid control members has an open position in which fluid is permitted to flow through the respective valve, and a closed position in which fluid is prevented from flowing through the respective valve. Each one of the valves is configured to engage the fluid control member of the other one of the valves to move the fluid control member from the open position to the closed position upon detachment of the valves from one another.

In another aspect, a kit for administering catheterization treatment generally comprises a first tube and a second tube. The kit further comprises a first valve that is connected to the first tube in flow communication, wherein the first valve has a first rotating-type fluid control member. The kit also comprises a second valve that is connected to the second tube in flow communication and is attachable to the first valve. The second valve has a second rotating-type fluid control member. Each of the fluid control members has an open position in which fluid is permitted to flow through the respective valve, and a closed position in which fluid is prevented from flowing through the respective valve. Each one of the valves is configured to engage the fluid control member of the other one of the valves to move the fluid control member from the open position to the closed position upon detachment of the valves from one another.

In yet another aspect, a breakaway connector generally comprises a non-ferromagnetic first valve having a first housing and a first rotating-type fluid control member disposed at least in part within the first housing. The first housing has a pair of arms each having a plurality of gear teeth. The connector further comprises a non-ferromagnetic second valve that is identical and attachable to the first valve. The second valve has a second housing and a second rotating-type fluid control member disposed at least in part within the second housing. The second housing has a pair of arms each with a plurality of gear teeth. Each of the fluid control members comprises a gear arrangement, and has an open position and a closed position within its respective housing. The first pair of arms is configured to engage its gear teeth with the gear arrangement of the second fluid control member to move the second fluid control member from the open position to the closed position upon detachment of the first valve from the second valve. The second pair of arms is configured to engage its gear teeth with the gear arrangement of the first fluid control member to move the first fluid control member from the open position to the closed position upon detachment of the second valve from the first valve.

BRIEF DESCRIPTION OF THE DRAWINGS

Corresponding reference characters indicate corresponding parts throughout the several views of the drawings.

DETAILED DESCRIPTION OF THE DRAWINGS

According to aspects of the disclosure, a breakaway connector is provided which overcomes at least some of the deficiencies of the conventional arrangements described above. More particularly, according to some aspects of the disclosure, the breakaway connector has a pair of valves that mate with one another to establish a fluid flow path through the connector, and the valves are identical to facilitate reducing costs associated with fabricating the connector. Moreover, in other aspects of the disclosure, the breakaway connector is fabricated without ferromagnetic material (e.g., the connector may be fabricated from a polycarbonate material and/or an acrylonitrile butadiene styrene (ABS) material), thereby permitting use of the connector in magnetic resonance imaging (MRI) settings. Additionally, in further aspects of the disclosure, the breakaway connector is configured for disconnecting a pair of tubes in response to at least one of the tubes being pulled, and the connector is configured to maintain the sterility of the fluid system and prevent fluid loss from either of the tubes upon such disconnection. Furthermore, in some aspects of the disclosure, the breakaway connector is configured with an optimized breakaway force (or tensile force) requirement for disconnecting a pair of tubes at the connector with minimal discomfort to the patient and minimal damage to the associated tubes.

Practically speaking, aspects of the connector disclosed herein can facilitate reducing equipment costs to hospitals, reducing waste of costly medication, improving patient safety, and improving nursing efficiency. This could lead to an overall improvement in care quality, as well as a net financial benefit to patients, care providers, and device manufacturers. These features will become more apparent with reference to the accompanying drawings.

Figure 1:
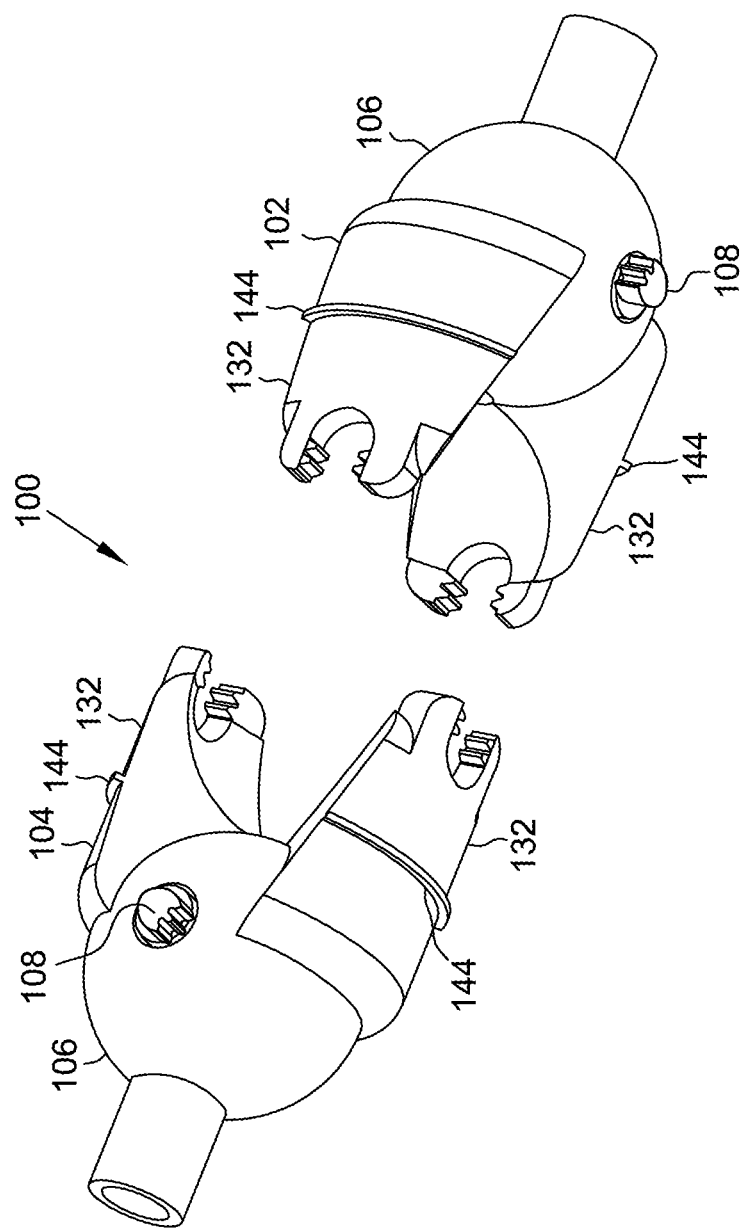
FIG. 1 is a perspective view of a breakaway connector having a pair of valves that mate with one another to establish a fluid flow path through the connector.
Figure 2:
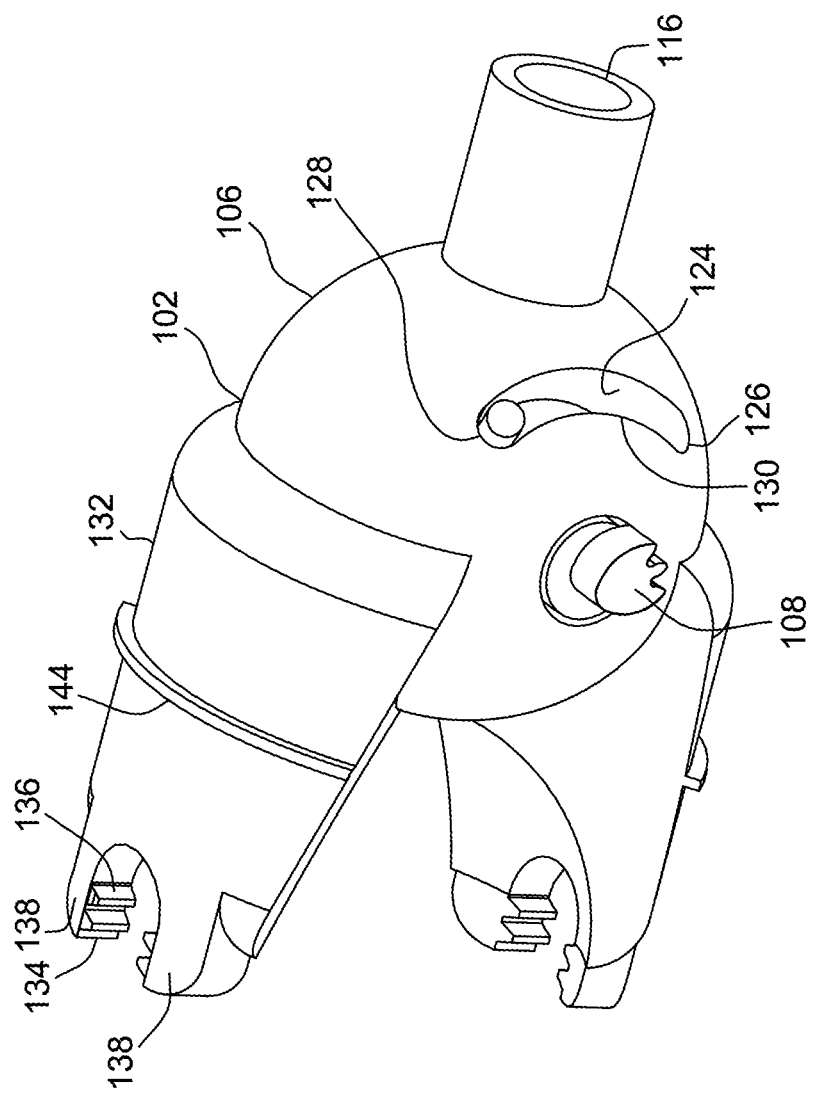
FIG. 2 is a back perspective view of one of the valves of the connector of FIG. 1, the other valve being identical.
Figure 3:
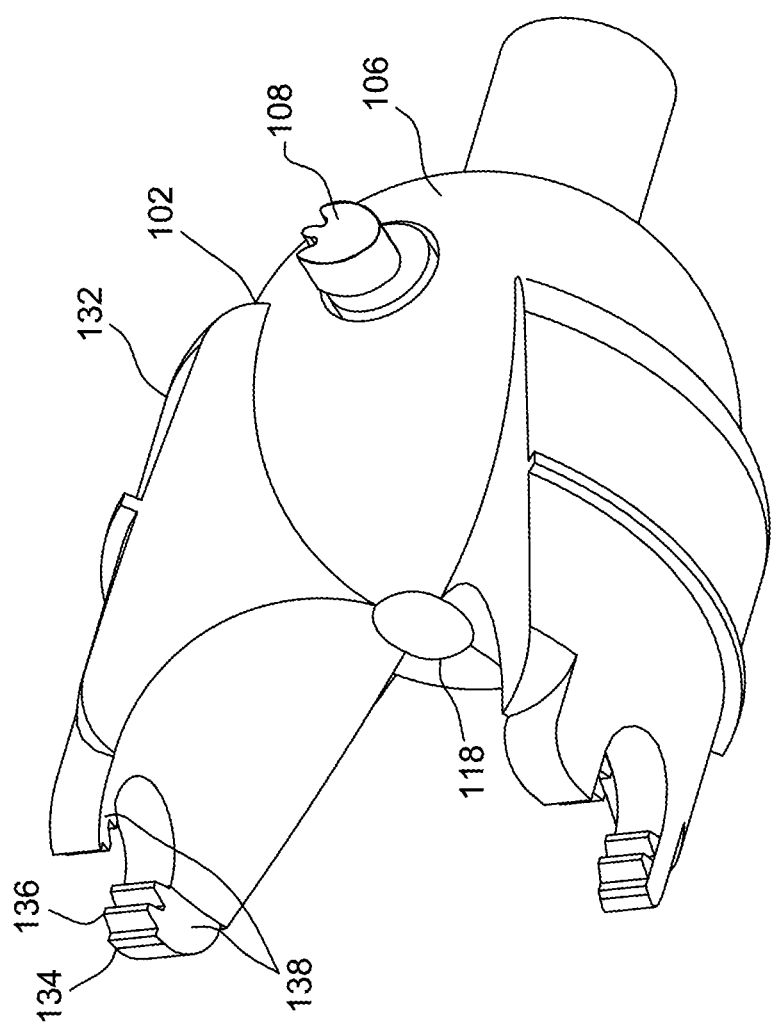
FIG. 3 is a front perspective view of the valve of FIG. 2.
Figure 4:
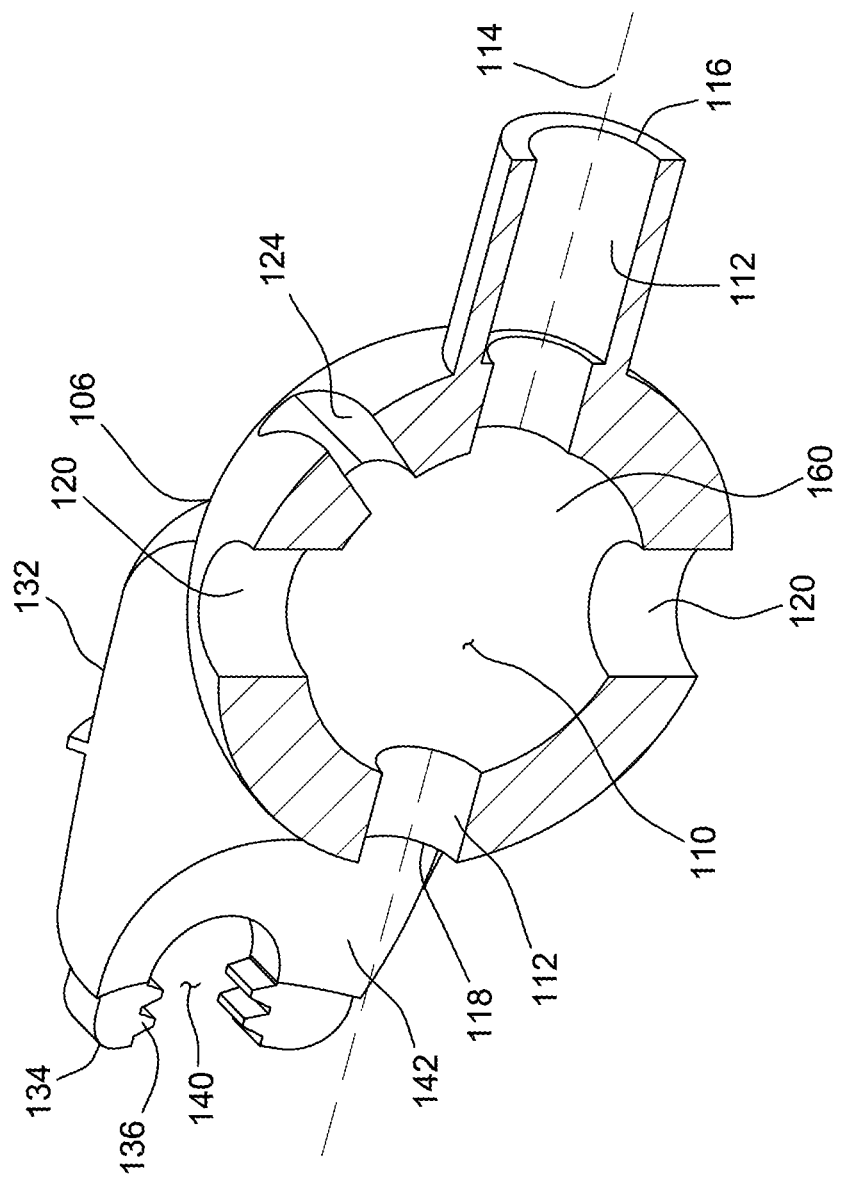
FIG. 4 is a sectional view of a housing of the valve of FIG. 2.

FIG. 1 illustrates one suitable embodiment of a breakaway connector, indicated generally at 100. The connector 100 has a first valve 102 and a second valve 104 that are configured to mate with one another to establish fluid flow through the connector 100 across the valves 102, 104. Particularly, as set forth in more detail below, attaching the valves 102, 104 together automatically opens both of the valves 102, 104, and detaching the valves 102, 104 from one another automatically closes both of the valves. In other contemplated embodiments, the connector 100 may have any number of valves that attach to, and detach from, one another in any suitable manner and that are fabricated from any suitable material that facilitates enabling the connector 100 to function as described herein.

With reference now to FIGS. 2-5, each of the valves 102, 104 has a housing 106 and a fluid control member 108 disposed at least in part within the housing 106. Notably, in the illustrated embodiment, the structural configuration of the first valve 102 is identical to that of the second valve 104 (i.e., the housing 106 and the fluid control member 108 of the first valve 102 are not structurally distinguishable from the housing 106 and the fluid control member 108 of the second valve 104). In this manner, a single valve design is used to fabricate both the first valve 102 and the second valve 104, thereby reducing costs associated with manufacturing the connector 100 as a whole. Thus, while the structural configuration of only the first valve 102 is set forth in detail below, it is understood that the second valve 104 is configured in the same manner.

The illustrated housing 106 of the first valve 102 defines an interior, substantially spherical chamber 110 (having a diameter). Extending through the housing 106, and in communication with the chamber 110, are diametrically opposed conduit segments 112 that essentially form a disjointed conduit across the chamber 110 along a flow axis 114 from a distal port 116 to a proximal port 118. Also extending through the housing 106 in communication with the chamber 110 are diametrically opposed sleeve segments 120 that essentially form a disjointed sleeve across the chamber 110, as well as a channel 124 having a first end 126, a second end 128, and an arcuate body 130 extending from the first end 126 to the second end 128.

Moreover, the housing 106 has on its exterior at least one arm 132 that extends substantially parallel to the flow axis 114. In the illustrated embodiment, for example, the housing 106 has a pair of arms 132 that are substantially diametrically opposed relative to the chamber 110. In other embodiments, however, the housing 106 may have any suitable number of arms 132 extending in any suitable manner (e.g., the housing 106 may have only one arm 132 in some embodiments).

Each arm 132 of the housing 106 has a distal end 134 and at least one gear tooth 136 formed at the distal end 134. In the illustrated embodiment, for example, each arm 132 has at its distal end 134 a pair of spaced-apart fingers 138 in a fork-type formation that defines a generally U-shaped receiving space 140, and each finger 138 has a plurality of gear teeth 136 extending into the receiving space 140. Additionally, each of the illustrated arms 132 has a substantially smooth inner surface 142 that curves about the flow axis 114. In other embodiments, each arm 132 may have any suitable gearing arranged in any suitable manner that facilitates enabling the arm(s) 132 to function as described herein.

Optionally, each arm 132 may also have suitable attachment indicia on its exterior to facilitate indicating when the first valve 102 has been completely attached to the second valve 104 in the manner set forth below. For example, to indicate complete attachment of the first valve 102 to the second valve 104, each of the illustrated arms 132 has a band 144 (in the form of a raised surface) oriented on a plane that is substantially perpendicular to the flow axis 114. As such, when mating the valves 102, 104 together to establish a fluid flow path through the connector 100, the valves 102, 104 are said to be completely attached when the bands 144 of the arms 132 of the first valve 102 are aligned with the bands 144 of the arms 132 of the second valve 104 to collectively form a single, annular band about the entire connector 100. In other embodiments, however, the attachment indicia may alternatively include a depressed surface, a distinct color, or other suitable visual or tactile indicator of complete attachment.

Figure 5:
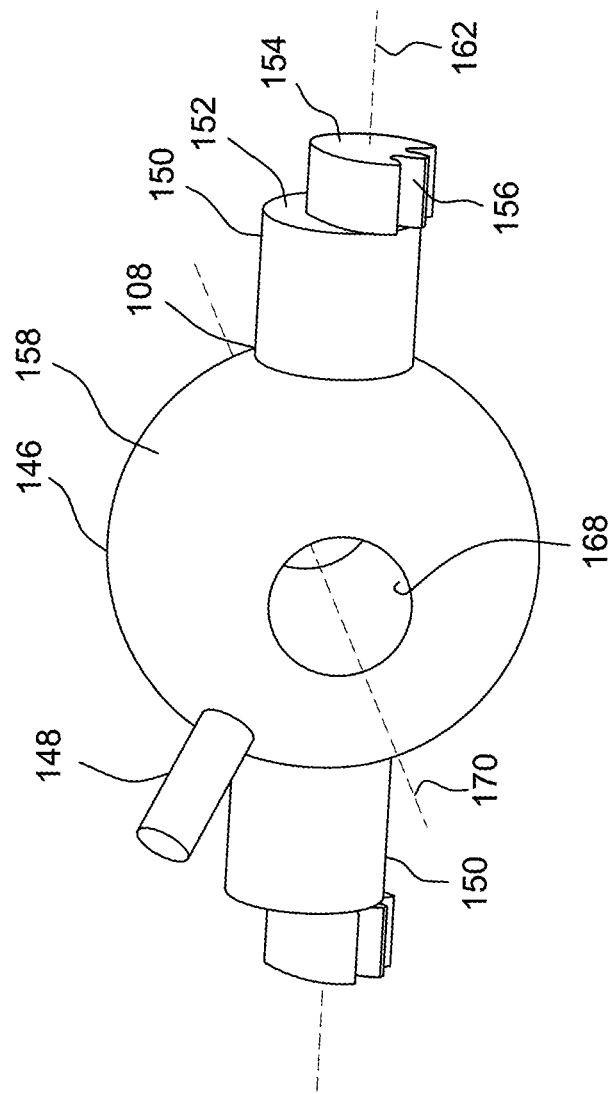
FIG. 5 is a perspective view of a fluid control member of the valve of FIG. 2.

With reference now to FIG. 5, the fluid control member 108 of the first valve 102 is a rotating-type control member. More specifically, the fluid control member 108 has a substantially spherical ball 146 (having a diameter), a pin 148 extending from the ball 146, and a pair of diametrically opposed stems 150 extending from the ball 146. Each stem 150 has a distal end 152 and a gear 154 (e.g., at least one gear tooth 156) formed on, or fixedly attached to, the stem 150 at the distal end 152. Moreover, the ball 146 has an intermediate conduit 168 that extends substantially diametrically across the ball 146 (and substantially perpendicular to a pivot axis 162 that extends centrally along the stems 150), and the intermediate conduit 168 has an intermediate axis 170 along which fluid can flow. Notably, in other contemplated embodiments, the fluid control member 108 may be any suitable rotating-type control member (e.g., the fluid control member 108 may have a generally cylindrical shape, instead of the ball shape of the illustrated embodiment).

In this manner, the fluid control member 108 is configured to substantially mirror the interior shape of the housing 106. More specifically, the ball 146 is sized to substantially mirror the shape of the chamber 110; each stem 150 is sized to fit within one of the sleeve segments 120; and the pin 148 is sized to extend into the channel 124. With respect to the ball 146 in particular, the ball 146 has an exterior surface 158 that is sized to seat in fluid-tight (yet slidable) abutment against an interior surface 160 of housing 106 that defines the chamber 110. Suitably, the interior surface 160 of the housing 106 and/or the exterior surface 158 of the ball 146 may be subjected during fabrication to a treatment that renders at least one of them either hydrophobic or hydrophilic, thereby facilitating a seal of the space between the surfaces 158, 160 to prevent fluid ingress between the surfaces 158, 160. In its fully assembled condition (i.e., when the fluid control member 108 is disposed within the housing 106), each valve 102, 104 has the ball 146 situated within the chamber 110 such that the pin 148 extends into the channel 124 and such that each of the stems 150 extends through one of the sleeve segments 120 to locate the gears 154 outside of the housing 106.

Referring now to FIGS. 6-10, the cooperative function of the valves 102, 104 will be described. With each of the valves 102, 104 fully assembled, a first tube may be suitably connected to the distal port 116 of the first valve 102, and a second tube may be suitably connected to the distal port 116 of the second valve 104. The tubes are automatically joined in fluid flow communication with one another by attaching the first valve 102 to the second valve 104 as set forth in more detail below. That said, due to the configuration of the valves 102, 104 set forth above, fluid flow through each of the tubes can be automatically stopped upon detachment of the first valve 102 from the second valve 104.

Figure 6:
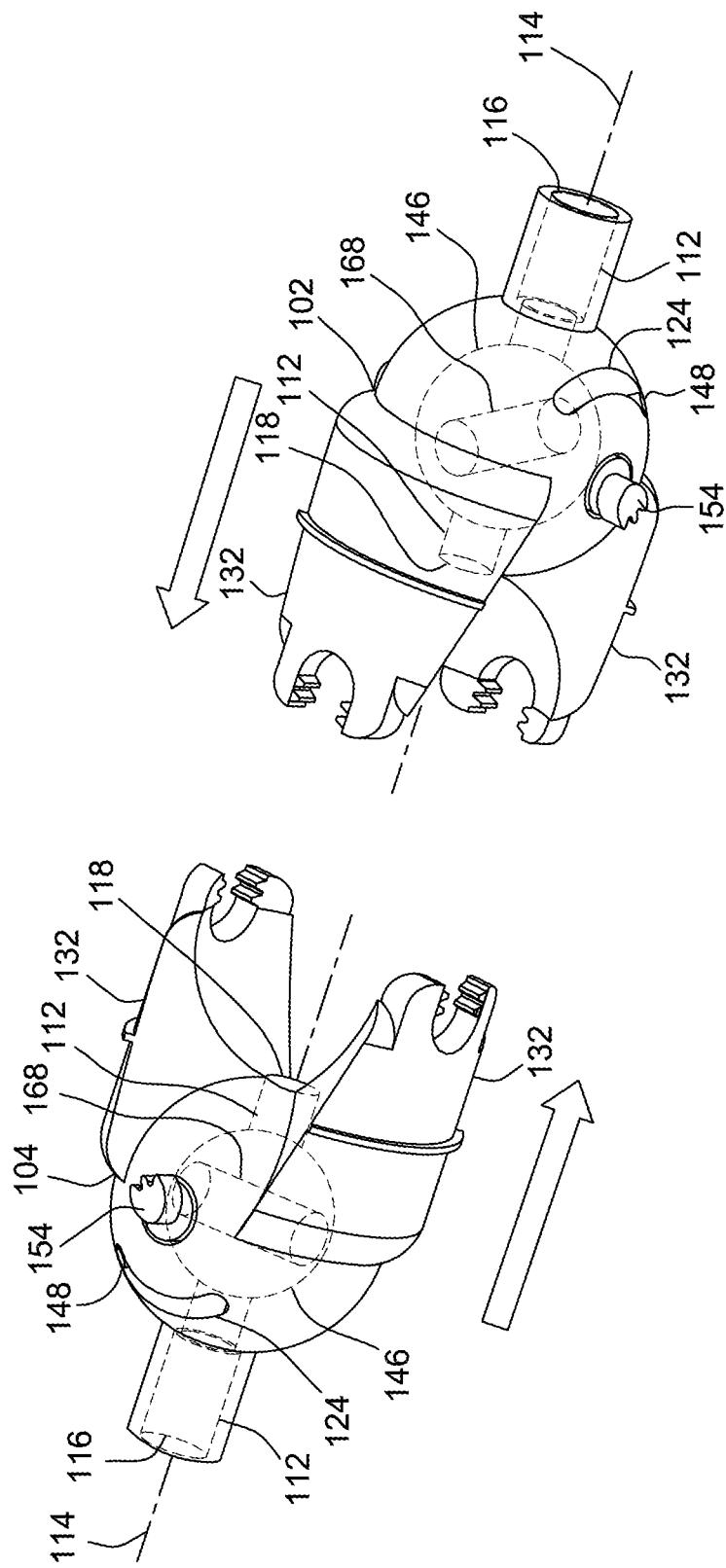
FIG. 6 is a perspective view of the connector of FIG. 1 with the valves completely detached from one another.
Figure 7:
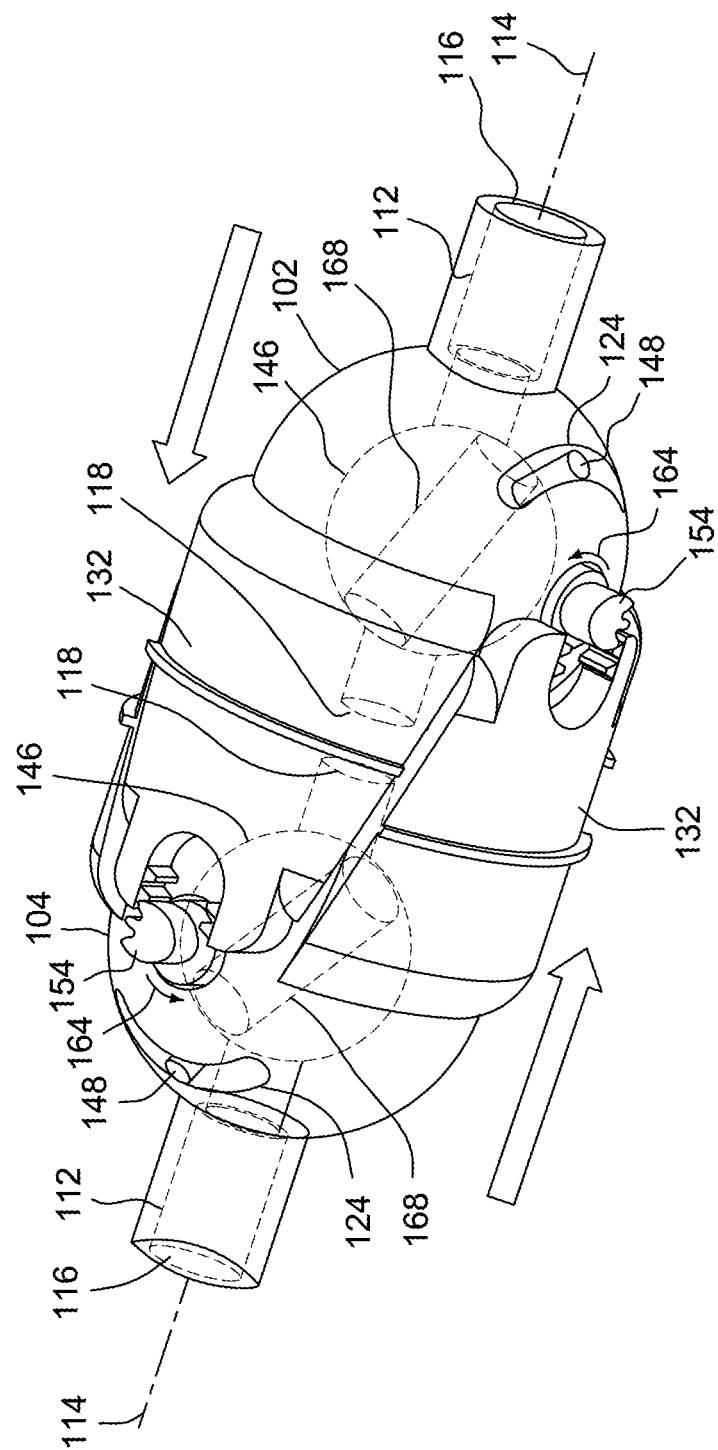
FIG. 7 is a perspective view of the connector of FIG. 1 with the valves partially attached to one another.
Figure 8:
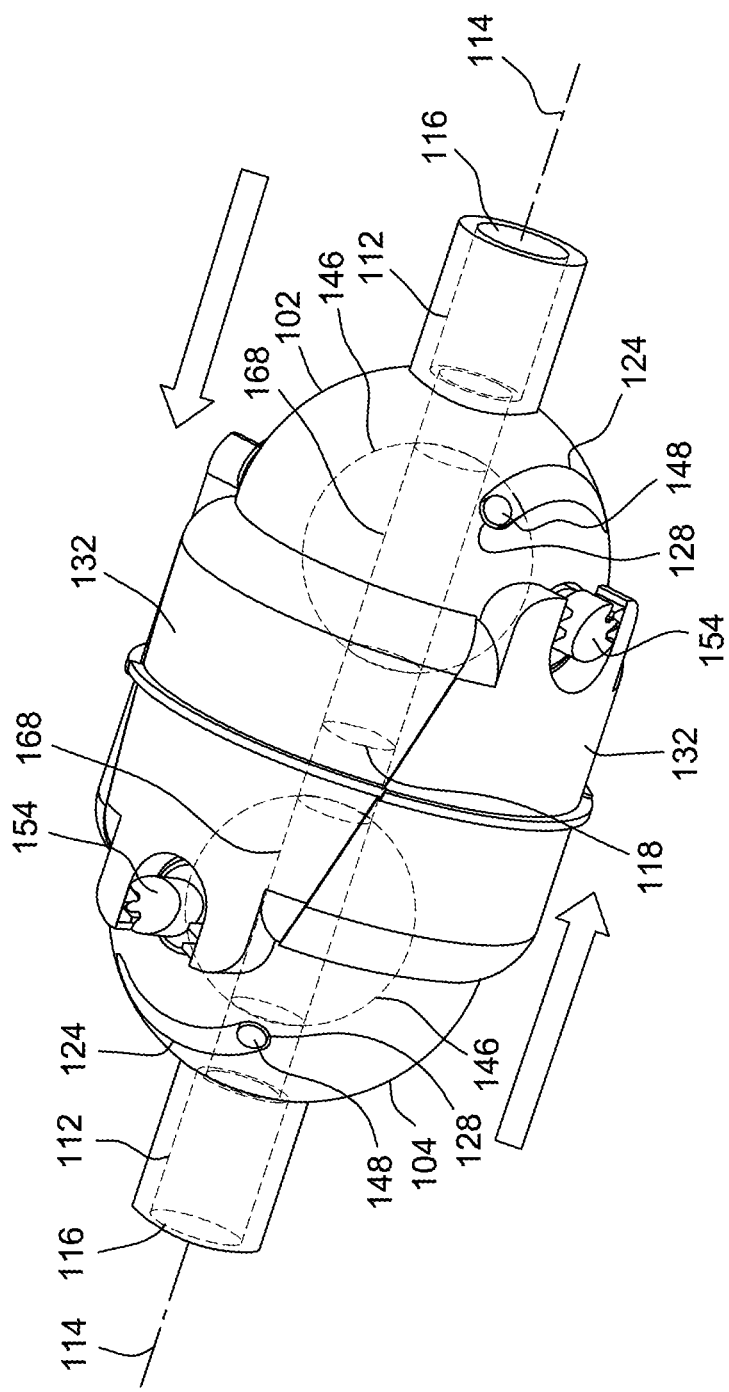
FIG. 8 is a perspective view of the connector of FIG. 1 with the valves completely attached to one another.

With particular reference to FIGS. 6-8, when attaching the valves 102, 104 to one another, the first valve 102 is mated with the second valve 104. The arms 132 of the first valve 102 receive the gears 154 of the second valve 104 in the receiving space 140 such that the gear teeth 136 of the first valve 102 engage the respective gear teeth 156 of the second valve 104. Likewise, the arms 132 of the second valve 104 receive the gears 154 of the first valve 102 in the receiving space 140 such that the gear teeth 136 of the second valve 104 engage the respective gear teeth 156 of the first valve 102. Because each valve 102, 104 is symmetrical across a plane on which its flow axis 114 lies (e.g., because the opposing halves of each valve 102, 104 are identical), each valve 102, 104 has a somewhat multirotational attachment capability, in that each valve 102, 104 is capable of attaching in more than one rotational orientation about its respective flow axis 114.

Upon engagement of the gear teeth 136, 156, each of the fluid control members 108 pivots within its housing 106 about a pivot axis 162 (shown in FIG. 5). More specifically, the gears 154 rotate in a first direction 164, such that the stems 150 and, therefore, the ball 146 are caused to pivot about the pivot axis 162 in the first direction 164 within the housing 106. As the ball 146 pivots within the chamber 110, the pin 148 slides along the channel 124 from the first end 126 toward the second end 128 of the channel 124, such that the second end 128 functions as a stop member for limiting the pivot range of the ball 146. In other words, when the pin 148 contacts the second end 128 of the channel 124, the fluid control member 108 is said to be in a first position (FIG. 8) at which further pivoting of the ball 146 in the first direction 164 is prevented.

Notably, for each of the valves 102, 104, the intermediate conduit 168 is oriented in its extension through the ball 146 such that, in the first position of the fluid control member 108, the intermediate conduit 168 is in flow communication with the conduit segments 112 of the housing 106. In other words, the intermediate conduit 168 is coaxial with the conduit segments 112 of the housing 106 (e.g., the intermediate axis 170 is oriented substantially parallel to and collinear with the flow axis 114) such that fluid is permitted to flow between the conduit segments 112 via the intermediate conduit 168. The first valve 102 and the second valve 104 are each said to be open in the first position of their respective fluid control members 108. When the valves 102, 104 are completely attached to one another and are open, fluid is permitted to flow through the connector 100 from the distal port 116 of the first valve 102 through the distal port 116 of the second valve 104, or vice versa.

Figure 9:
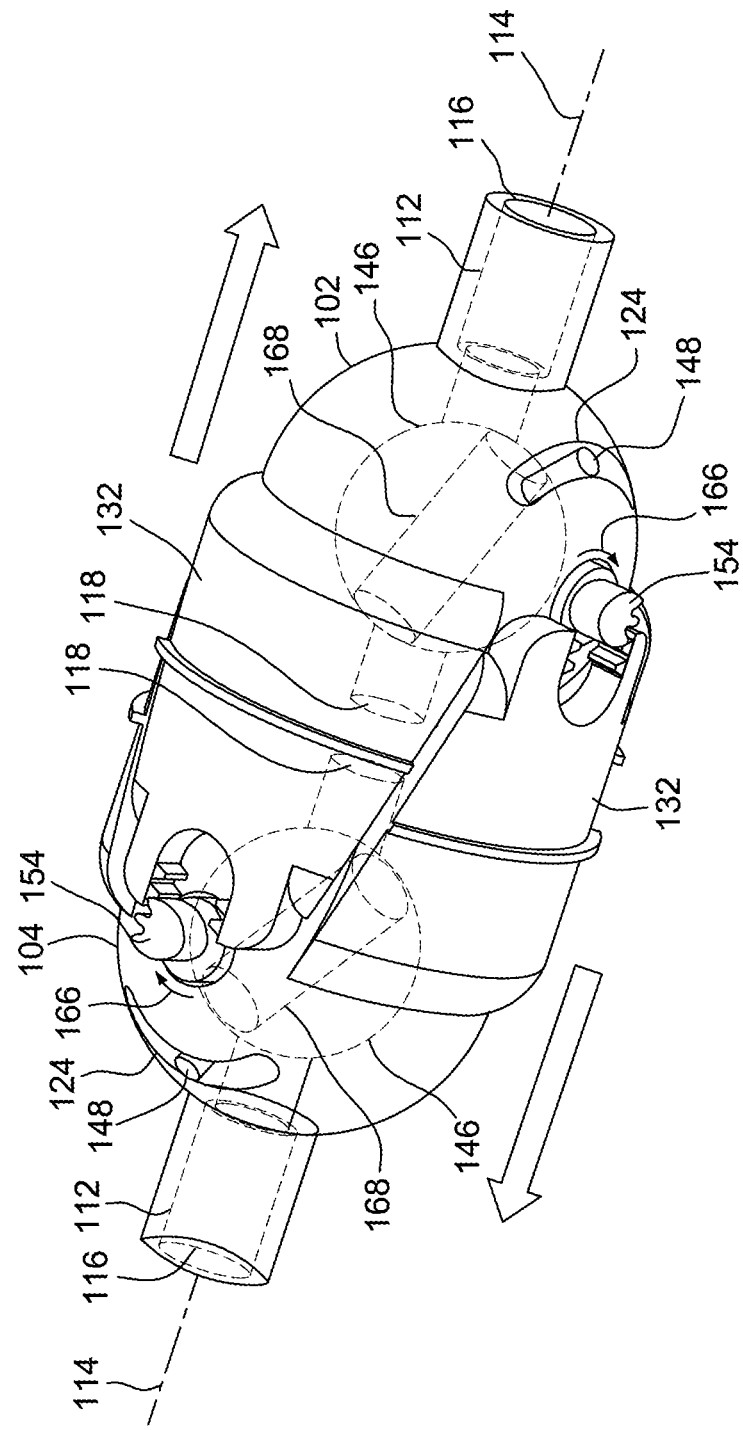
FIG. 9 is a perspective view of the connector of FIG. 1 with the valves partially detached from one another.
Figure 10:
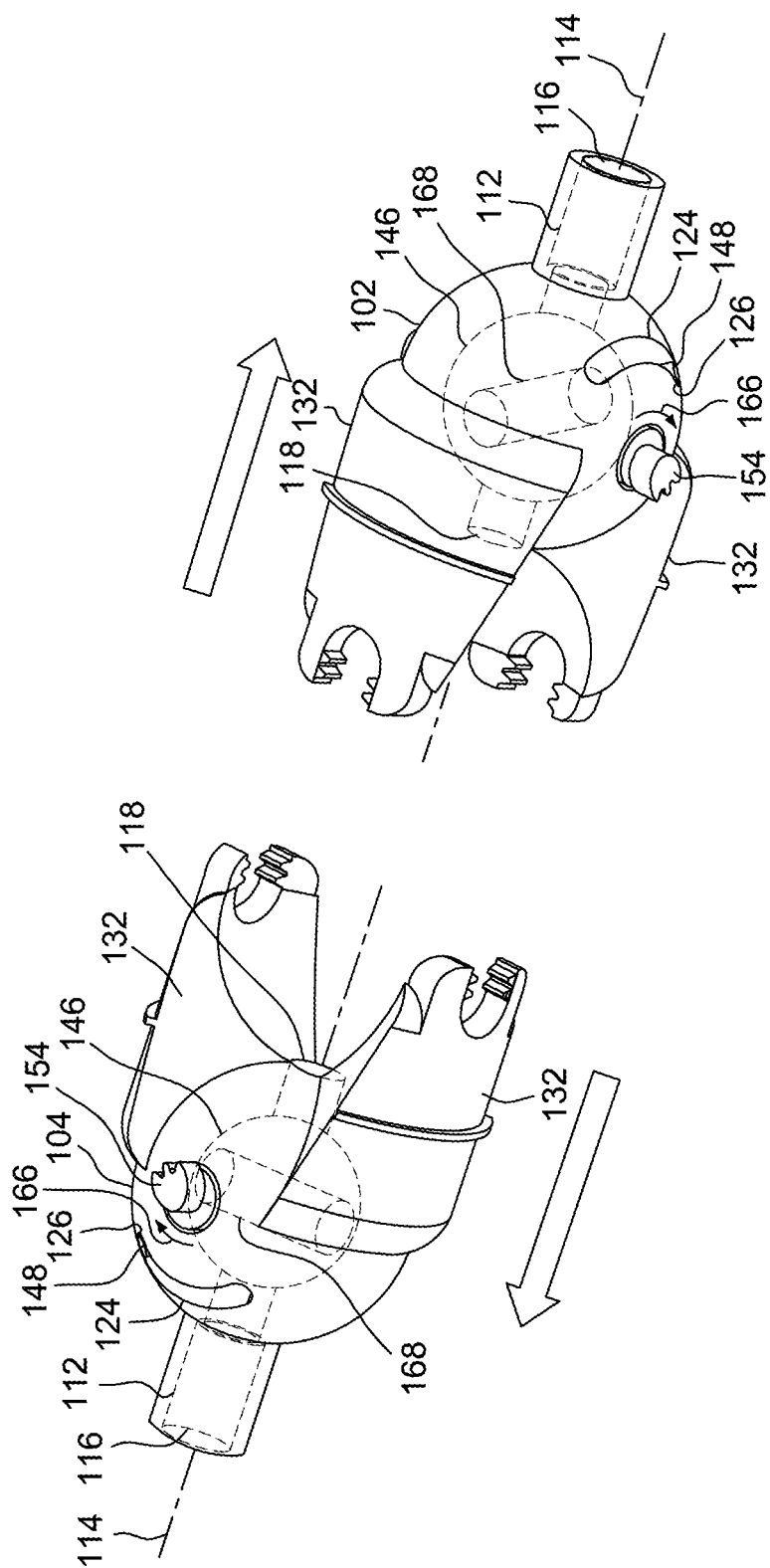
FIG. 10 is a perspective view of the connector of FIG. 1 with the valves completely detached from one another.

Referring now to FIGS. 9 and 10, upon detachment of the first and second valves 102, 104 from one another (e.g., if the tube associated with one of the valves 102, 104 is inadvertently pulled), the gears 154 withdraw from their respective receiving spaces 140 such that the gear teeth 136 rotate their cooperating gear teeth 156 in a second direction 166. Thus, for each respective valve 102, 104, the stems 150 and, therefore, the ball 146 is caused to pivot about its pivot axis 162 in the second direction 166 within the housing 106. Upon complete detachment of the valves 102, 104, the pin 148 of each valve 102, 104 contacts the first end 126 of its respective channel 124, and the fluid control member 108 of each valve 102, 104 is said to be in a second position (FIG. 10) at which further pivoting of the respective ball 146 in the second direction 166 is prevented.

Notably, when each fluid control member 108 is in the second position (i.e., when the pin 148 contacts the first end 126 of the channel 124), the intermediate conduit 168 is no longer coaxial with the conduit segments 112 of the associated housing 106 (e.g., the intermediate axis 170 is instead oriented substantially perpendicular to the flow axis 114) such that fluid is not permitted to flow between the conduit segments 112 via the intermediate conduit 168. The first valve 102 is said to be closed in the second position of the fluid control member 108). When the valves 102, 104 are closed, fluid flow out of the respective proximal ports 118 is prevented by virtue of the orientation of the respective intermediate conduits 168 relative to their associated conduit segments 112. In this manner, the connector 100 is configured such that the valves 102, 104 can detach from one another under the influence of an external pulling force on their respective tubes so as to reduce patient discomfort, minimize damage to the tubes, maintain a sterile fluid system, and prevent fluid loss. Suitably, the valves 102, 104 can be reattached to one another as desired in order to re-establish fluid flow through the connector.

Optionally, the width of the channel 124 and the girth of the pin 148 may be selected to suit a desirable frictional interaction between the pin 148 and the channel 124 in order to establish the ease at which the valves 102, 104 are attachable to, and detachable from, one another. More specifically, in one embodiment, the channel 124 may be made narrower near its center than at its ends 126, 128 such that, when the pin 148 slides along the channel 124, the pin 148 experiences more resistance in the middle region of the channel 124 than near the ends 126, 128, thereby making it more difficult to detach the valves 102, 104 from one another. Optionally, the channel 124 may be lined with a resilient material by which the width of the channel 124 is varied, and the resilient material may compress at the narrower region(s) of the channel 124 as the pin 148 slides along the channel 124 to facilitate suitably restricting movement of the pin 148 therealong. Or, alternatively, the pin 148 may be made of a resilient material that compresses as the pin 148 slides along the channel 124 of varying width. Thus, the geometry and material choice of the pin 148 and/or the channel 124 are selectable to suit a desired pull force (or tensile force) requirement for detaching the first valve 102 from the second valve 104.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A breakaway connector comprising:
   a first valve having a first rotating-type fluid control member; and
   a second valve that is attachable to the first valve and has a second rotating-type fluid control member,
   wherein each of the fluid control members has an open position in which fluid is permitted to flow through the respective valve, and a closed position in which fluid is prevented from flowing through the respective valve, and
   wherein the first valve and the second valve are identical, and each one of the first and second valves is configured to engage the fluid control member of the other one of the valves to move the fluid control member from the open position to the closed position upon detachment of the valves from one another.

2. The breakaway connector set forth in claim 1 wherein the engagement is a geared engagement.

3. The breakaway connector set forth in claim 1 wherein each one of the valves is configured for multirotational attachment to the other one of the valves.

4. The breakaway connector set forth in claim 1 wherein each one of the valves are free of ferromagnetic materials.

5. The breakaway connector set forth in claim 1 wherein each one of the valves are configured with attachment indicia for indicating when the valves are completely attached to one another.

6. The breakaway connector set forth in claim 1 wherein each one of the valves comprises a pair of arms that engages the fluid control member of the other one of the valves.

7. The breakaway connector set forth in claim 6 wherein each of the arms of each one of the valves comprises a pair of fingers that defines a receiving space for receiving the fluid control member of the other one of the valves.

8. The breakaway connector set forth in claim 1 wherein each of the valves is configured to restrict the movement of its own fluid control member.

9. The breakaway connector set forth in claim 8 wherein each the valves is configured to frictionally restrict the movement of its own fluid control member.

10. The breakaway connector set forth in claim 1 wherein each one of the fluid control members is a ball-type fluid control member.

11. The breakaway connector set forth in claim 1 wherein each one of the fluid control members is cylindrical.

12. The breakaway connector set forth in claim 1 wherein each one of the valves has a housing, such that each one of the fluid control member and the housing of the each one of the valves deviates from a prism of revolution to facilitate providing an interference fit therebetween that is adjustable to tune a breakaway force of the valves from one another.

13. The breakaway connector set forth in claim 12 further comprising a control structure that is adjustable to tune the breakaway force.

14. The breakaway connector set forth in claim 13 wherein the control structure is a set screw that is adjustable to tune the breakaway force for the valves by modulating a force requirement for rotating the fluid control member of the at least one of the fluid control member and the housing.

15. The breakaway connector set forth in claim 14 wherein the set screw directly contacts the fluid control member of the at least one of the fluid control member and the housing.

16. The breakaway connector set forth in claim 14 wherein the set screw is configured such that adjusting the set screw at least one of compresses and relieves compression of the at least one of the fluid control member and the housing against one another.

17. A kit for administering catheterization treatment, the kit comprising:
    a first tube;
    a second tube;
    a first valve that is connected to the first tube in flow communication, wherein the first valve has a first rotating-type fluid control member; and
    a second valve that is connected to the second tube in flow communication and is attachable to the first valve, the second valve having a second rotating-type fluid control member,
    wherein each of the fluid control members has an open position in which fluid is permitted to flow through the respective valve, and a closed position in which fluid is prevented from flowing through the respective valve, and
    wherein each one of the valves is configured to engage the fluid control member of the other one of the valves at two, spaced apart locations to move the fluid control member from the open position to the closed position upon detachment of the valves from one another.

18. The kit set forth in claim 17 wherein each one of the valves comprises a pair of arms, each of the arms comprising a pair of fingers that defines a receiving space for receiving the fluid control member of the other one of the valves.

19. A breakaway connector comprising:
    a non-ferromagnetic first valve having a first housing and a first rotating-type fluid control member disposed at least in part within the first housing, wherein the first housing has a pair of arms each having a plurality of gear teeth; and
    a non-ferromagnetic second valve that is identical and attachable to the first valve, wherein the second valve has a second housing and a second rotating-type fluid control member disposed at least in part within the second housing, the second housing having a pair of arms each with a plurality of gear teeth,
    wherein each of the fluid control members comprises a gear arrangement, and has an open position and a closed position within its respective housing, such that the first pair of arms is configured to engage its gear teeth with the gear arrangement of the second fluid control member to move the second fluid control member from the open position to the closed position upon detachment of the first valve from the second valve, and such that the second pair of arms is configured to engage its gear teeth with the gear arrangement of the first fluid control member to move the first fluid control member from the open position to the closed position upon detachment of the second valve from the first valve.

* * * * *